(12) United States Patent
Ngo et al.

(10) Patent No.: US 12,295,530 B2
(45) Date of Patent: May 13, 2025

(54) HAND WASHING, DISINFECTION AND AUTOMATIC MASSAGE MACHINE, AND METHOD OF OPERATING THE SAME

(71) Applicant: Thuan Dac Ngo, Ho Chi Minh (VN)

(72) Inventors: Thuan Dac Ngo, Ho Chi Minh (VN); Ha Viet Hoang, Ho Chi Minh (VN); Tuan Minh Pham, Ho Chi Minh (VN)

(73) Assignee: Thuan Dac Ngo, Ho Chi Minh (VN)

( * ) Notice: Subject to any disclaimer, the term of this patent is extended or adjusted under 35 U.S.C. 154(b) by 769 days.

(21) Appl. No.: 17/456,594

(22) Filed: Nov. 26, 2021

(65) Prior Publication Data

US 2022/0175197 A1 Jun. 9, 2022

(30) Foreign Application Priority Data

Dec. 4, 2020 (VN) ................ 1-2020-07046

(51) Int. Cl.
| | |
|---|---|
| *A61H 9/00* | (2006.01) |
| *A47K 7/04* | (2006.01) |
| *A61H 7/00* | (2006.01) |
| *A61L 2/00* | (2006.01) |
| *A61L 2/10* | (2006.01) |
| *A47K 10/48* | (2006.01) |

(52) U.S. Cl.
CPC ............ *A47K 7/04* (2013.01); *A61H 7/004* (2013.01); *A61L 2/0088* (2013.01); *A61L 2/10* (2013.01); *A47K 10/48* (2013.01); *A61H 2201/105* (2013.01); *A61H 2201/1638* (2013.01); *A61H 2201/5046* (2013.01); *A61H 2205/065* (2013.01); *A61L 2202/11* (2013.01); *A61L 2202/14* (2013.01); *A61L 2202/17* (2013.01)

(58) Field of Classification Search
CPC ...... A61H 7/002; A61H 35/00; A61H 35/006; A61H 2205/12; A61H 2205/065; A61H 15/00; A61H 2009/0042; A61H 9/0021; A47K 7/026; A47K 7/04; A47K 7/02; A47K 3/022; A47K 2210/00
See application file for complete search history.

(56) References Cited

U.S. PATENT DOCUMENTS

| | | | | |
|---|---|---|---|---|
| 2,248,205 A | * | 7/1941 | Stobbe ................. | A61H 35/00 4/606 |
| 2,814,081 A | * | 11/1957 | Stevenson ............. | A47K 7/04 422/292 |
| 2,952,859 A | * | 9/1960 | Alcamo ................. | A61B 90/80 4/606 |

(Continued)

FOREIGN PATENT DOCUMENTS

VN  1-2020-07046  12/2020

*Primary Examiner* — Justine R Yu
*Assistant Examiner* — Christopher E Miller (57) ABSTRACT

The present invention is to provide a hand washing, disinfection and automatic massage machine. The machine is housed in a case, in which the washing and disinfectant compartment, a wastewater treatment compartment can be maintained as a control hand washing, sanitizing and massaging environment. The water can be supplied by a water pump and wastewater treatment compartment and the disinfection process is provided by UV lamps. In addition, the present invention provides a method of operating a hand washing, disinfection and automatic massage machine.

13 Claims, 6 Drawing Sheets

(56) References Cited

U.S. PATENT DOCUMENTS

| | | | | |
|---|---|---|---|---|
| 3,439,370 A * | 4/1969 | McLaughlin | A47K 7/04 | |
| | | | 15/4 | |
| 3,699,984 A * | 10/1972 | Davis | A61L 2/18 | |
| | | | 134/199 | |
| 3,757,806 A * | 9/1973 | Bhaskar | A61C 17/028 | |
| | | | 134/191 | |
| 3,918,117 A * | 11/1975 | Plante | A47K 7/04 | |
| | | | 15/88.3 | |
| 3,918,987 A * | 11/1975 | Kopfer | A61B 90/80 | |
| | | | 601/166 | |
| 4,402,331 A * | 9/1983 | Taldo | A61B 90/80 | |
| | | | 134/178 | |
| 4,465,522 A * | 8/1984 | Taldo | A61B 90/00 | |
| | | | 134/17 | |
| 4,688,585 A * | 8/1987 | Vetter | B08B 3/006 | |
| | | | 118/679 | |
| 4,817,651 A * | 4/1989 | Crisp | A61B 90/80 | |
| | | | 604/289 | |
| 4,898,148 A * | 2/1990 | Urso | F25D 3/06 | |
| | | | 126/266 | |
| 4,925,495 A * | 5/1990 | Crisp | A61B 90/80 | |
| | | | 134/95.1 | |
| 5,241,953 A * | 9/1993 | Sykes | A61H 9/00 | |
| | | | 601/165 | |
| 5,522,411 A * | 6/1996 | Johnson | A47K 10/48 | |
| | | | 134/107 | |
| 5,924,148 A * | 7/1999 | Flowers, Sr. | A47K 10/48 | |
| | | | 4/619 | |
| 6,039,703 A * | 3/2000 | Badilla | A61H 7/001 | |
| | | | 601/134 | |
| 6,161,227 A * | 12/2000 | Bargenquast | A47K 5/1217 | |
| | | | 134/58 R | |
| 10,542,809 B2 * | 1/2020 | Maletti | A45D 19/04 | |
| 2005/0203447 A1* | 9/2005 | Pisani | A61H 9/00 | |
| | | | 601/55 | |
| 2007/0213877 A1* | 9/2007 | Hart | G07C 9/22 | |
| | | | 700/282 | |
| 2008/0099050 A1* | 5/2008 | Barnhill | A61B 90/80 | |
| | | | 134/18 | |
| 2012/0186011 A1* | 7/2012 | Wright | A47K 10/48 | |
| | | | 4/638 | |
| 2013/0136669 A1* | 5/2013 | Feldain | A47K 7/04 | |
| | | | 422/300 | |
| 2023/0233036 A1* | 7/2023 | Ouazzani | A47K 10/48 | |
| | | | 4/616 | |

* cited by examiner

HAND WASHING, DISINFECTION AND AUTOMATIC MASSAGE MACHINE, AND METHOD OF OPERATING THE SAME

FIELD OF THE INVENTION

The present invention relates to an automatic hand washer, especially its functions include disinfection and automatic massage; and method to operate the machine.

BACKGROUND ART

Currently the issue of hand hygiene before eating or before and after contacting, operating patients or regularly cleaning their hands in an environment with a high potential for infection is very important to help limit possibility of cross infection of pathogens from the outside into the human body. According to the World Health Organization, human hand hygiene is considered a "homemade vaccine". It is very simple and easy to implement due to cost effectiveness and life saving. Hand hygiene is the most important and effective way to prevent infection. There are two types of bacteria on the skin of the hands: resident bacteria and transient bacteria. The resident bacteria have low toxicity but it can cause toxicity through invasive procedures in patients. The transient bacteria are common pathogens of nosocomial infections, usually stay on the skin for on more than 28 hours and are easily removed by hand washing with soap.

Meanwhile, the Ministry of Health has issued a proper hand hygiene, including: step 1) wet palms with water, put soap on palms, rub palms together; step 2) rub one palm against the back of the other and vice versa; step 3) rub the palms together, interlace and squeeze fingers together; step 4) rub the backs of the fingers on the palms of the other hand and vice versa; step 5) rub the thumb of one hand against the palm of the other and vice versa; step 6) rub the fingertips into the palm of the other hand and vice versa, finally rinse your hands under wrist running water and dry your hand.

In the domestic and foreign markets there are many different types of equipment used for to hand washing and disinfection, located in public restrooms in places such as hospitals, shopping malls, restaurants, theaters, community areas etc. however, not many devices can provide high efficiency and low cost effectiveness.

Patent application CN210354482U discloses an intelligent hand washing box with body, the front of the body has two hand washing inlet holes, the inner wall surface of the top surface and both ends of the canister are provided with a disinfectant nozzle, the pipeline the disinfectant nozzle is connected to a disinfectant pipe, the pipeline the disinfectant is located in the inner wall of the body, an infrared sensor is installed at the center of the upper side of the body, an electrical cabinet is located at the bottom of the body, a single chip computer and integrated power source is electrically connected to the and of the single-chip microcomputer via a wire, the bottom is connected to the waste collection hopper liquid, the liquid outlet of a liquid wastes collection funnel is connected to a waste liquid discharge pipe. The disinfectant box is installed on one side of the hand washing box, the disinfectant box is composed of the liquid container and the holder for fixing the liquid container. The fixed bracket is fixed to the outer wall of the body of the hand washing box, a water pump is installed inside the liquid storage box, and the water pump liquid connector is connected to the pipe. A disinfectant solution is added to the top of the liquid container.

Patent application CN20982687U, discloses a fully automatic medical hand washing machine, having a chassis, a partition that is permanently installed on the back of the chassis. A controller is installed on the baffle and is connected to the external power supply, a tap is fixed on the upper back of the chassis, the water pipe is connected to the chassis, the water pipe is connected to the faucet, a de-agent addition divide. The sanitizer is permanently installed at the water outlet of the tap, a disinfectant supply device is fixed on the front surface of the baffle, and a disinfectant container is permanently clustered in the side surface. The front of the baffle, the surface of the disinfectant container is in contact with the water pump, the water pump outlet is connected to the disinfectant supply device via pipes and water tap, the substance supply device, the sterilizer and the water pump are both electrically connected to controller box.

Patent application CN208533640U, discloses a disinfectant hand washing device, composed of the body, disinfection tank, water pipes, characterized in that: the sterilization tank is installed on the body machine, the bottom of the sterilizer tank is equipped with a dynamic circuit connector switch that can activate the first time relay, the first time relay installed inside the machine body and lie under the disinfection tank. One end of the thimerosal output tube is installed at the top edge of the sterilization the other end is connected to the tank, the thimerosal is stored in the tank and the first electronic valve is provided on the thimerosal output tube. The first electronic valve is located inside the body of the machine and an output tube is installed on the body of the machine. The output pipe is located on top of the output thimerosal tube, the output tube connects to the water supply, on the output tube is supplied with the second solenoid valve. An air blower is installed at the top of the machine body, the blower has the outlet of the wind down in the vertical direction.

Patent application U.S. Pat. No. 6,141,811A, discloses an automatics hand washing device consisting of a housing containing a detergent supply. A pair of openings to receive hands and arms need to be cleaned. The openings define the axes along which the arm and hand can be inserted. A pair of opposite horizontal brushes are supplied adjacent to the openings and mounted for reciprocal motion so that they move perpendicular to the shaft. A control-engine is connected and drives the brush pair. The float valve mechanism is connected to the water supply to adjust the water level inside the machine. A heater is submerged in the wash water to heat the water waste. A water pump is installed in the housing and submerged in the wash water, a nozzle is mounted in the housing and is used to spray the wash water onto the brush, arm and hand, the water pump is connected to the nozzle. A flapper valve at the bottom of the device is used to drain dirty water after hand cleaning from the case.

It can be seen that the above inventions meet their specific purposes and requirements, however they do not use a washing and disinfection with integrated hand wipes, hand hygiene brooms, and not installed with clean water spray, soap solution, air drying and disinfectant solution through pipes with spray nozzles. Furthermore, the above inventions do not have an automatic wrist lock mechanism to keep water, soap solution, drying air and disinfectant solution in place, further, they do not provide a hand massage device and nor an UV lamp to disinfect the device after hand cleaning.

Therefore, it is essential to design automatic equipment with simple structure, fully automatic operation, easy to install and easy to use at a reasonable cost. Further, the installation can be anywhere, public or private properties, indoors, outdoors, hospital, schools, stadiums, etc. It is also necessary to design an automatic machine with a washing and disinfection with integrated hand wipes, hand sanitizer broom, and be installed with clean water spray modes, soap solution, drying air and disinfectant solution through pipes fitted with nozzles, helping to perform hand hygiene according to the guideline recommended by the Ministry of Health to prevent cross-contamination hand diseases.

It is also necessary to design an automatic hand wash machine, besides performing hand hygiene, there is also a hand massage device which soothes the hands.

It is also essential to design an automatic hand wash, disinfection and massage machine that uses additional UV lights to disinfect the wash chamber after each use.

The method and system disclosed in the present invention solve the above described problems.

SUMMARY OF THE INVENTION

The main purpose of the invention is to provide A hand washing, disinfection and automatic massage machine, comprising an LCD touch screen, signal LEDs, a support frame, a wrist lock controller, a movement controller, a washing and disinfection compartment, UV lamps, a wastewater treatment compartment, a water pump and air blower compartment, an energy source, and a controller.

Particularly, the hand washing, disinfection and automatic massage machine housed in a case; the LCD touch screen and the signal LEDs are installed in front of the case; the LCD touch screen displays warnings, reminders, instructions on hand washing steps and washing progress, settings during user cleaning and disinfection of hands; the signal LEDs indicates the operating status of the hand washing, disinfection and automatic massage machine; the support frame mechanically connected the wrist lock controller, the movement controller, the washing and disinfection compartment, the UV lamps, the wastewater treatment compartment, the water pump and air blower compartment, the energy source, and the controller; the wrist lock controller to open/close to prevent water, soap solution, air and disinfectant solution from going out the hand washing, disinfection and automatic massage machine during hand hygiene; the movement controller controls and directs the movement of the washing and disinfection compartment; the washing and disinfection compartment is used for washing, disinfecting and massaging hands; the UV lamps are responsible for disinfecting of the inside of the hand washing, disinfection and automatic massage machine; the wastewater treatment compartment to keep wastewater inside the hand washing, disinfection and automatic massage machine; the water pump and air blower compartment supplies clean water, soap, disinfectant solution and air to the washing and disinfection compartment for hand hygiene; the controller is programmed with software to control hand hygiene operations of the hand washing, disinfection and automatic massage machine.

The other purpose of the invention is to provide a method of operating a hand washing, disinfection and automatic massage machine including the following steps:

i) selecting setting parameters for the operation mode of said hand washing, disinfection and automatic massage machine; if users want to change the operation mode pre-programmed for the hand washing, disinfection and automatic massage machine follow step ii); otherwise perform step iii);

ii) setting parameters for the controller to control operation mode of the hand washing, disinfection and automatic massage machine through the setting keys on the interface of the LCD touch screen; the parameters set by the user shall not be less than the values of the pre-programmed parameters of the hand washing, disinfection and automatic massage machine;

iii) performing a cycle of hand hygiene and massage by the controller that transmits motion to the rotary bar and the thrust levers, to rotate movable plates and movable blades creating full opening on the wrist lock mechanisms for the users to insert their hands into the washing chamber; if the user's hands are in the correct position, the wrist lock mechanisms driven by the first motor causing the movable blades slowly radiate until they touch the user's hand, and the yellow light of said the signal LEDs will light up to indicate that said the hand washing, disinfection and automatic massage machine is performing the hand hygiene process; the washing and disinfection compartment performs the cycle of hand hygiene and massage; if the user's hand not properly positioned, an error message displayed on the interface of the LCD touch screen;

iv) cleaning the machine and get ready for the next hand hygiene process by controlling the wrist locking mechanisms so that the movable blades to radiate completely to close the wrist lock mechanisms; next, spinning the fourth motor, the fifth motor and the sixth motor at high speed to cause water to splash from the wiper cluster, the brush cluster and the massage cluster; finally, turning UV lamps on for a preset time to disinfect inside the washing chamber; at the end of the hand hygiene process, the UV lamps are off, and the green light of the signal LEDs light up to indicate the hand washing, disinfection and automatic massage machine is ready for next hand hygiene; for the case of a user performing step ii), the controller adjusts the hand washing, disinfection and automatic massage machine to the default programmed operation mode.

The other purpose of the invention is to create the hand washing, disinfection and automatic massage machine besides performing hand hygiene, there is also a hand massage, which helps create comfortable for hands.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

References will now be made in detail to the invention, examples of which are illustrated in the accompanying drawings. The invention is intended to cover alternatives, modifications and equivalents, which may be included within the spirit and scope of the invention as defined by the appended claims. In the following detailed description of the present invention, numerous specific details are set forth in order to provide a thorough understanding of the present invention. However, it would be obvious to one of ordinary skills in the art at the time of the invention was made, it may be practiced without these specific details. In other instances, well-known methods, procedures, components, and circuits have not been described in detail so as not to unnecessarily obscure aspects of the present invention.

Figure 1:
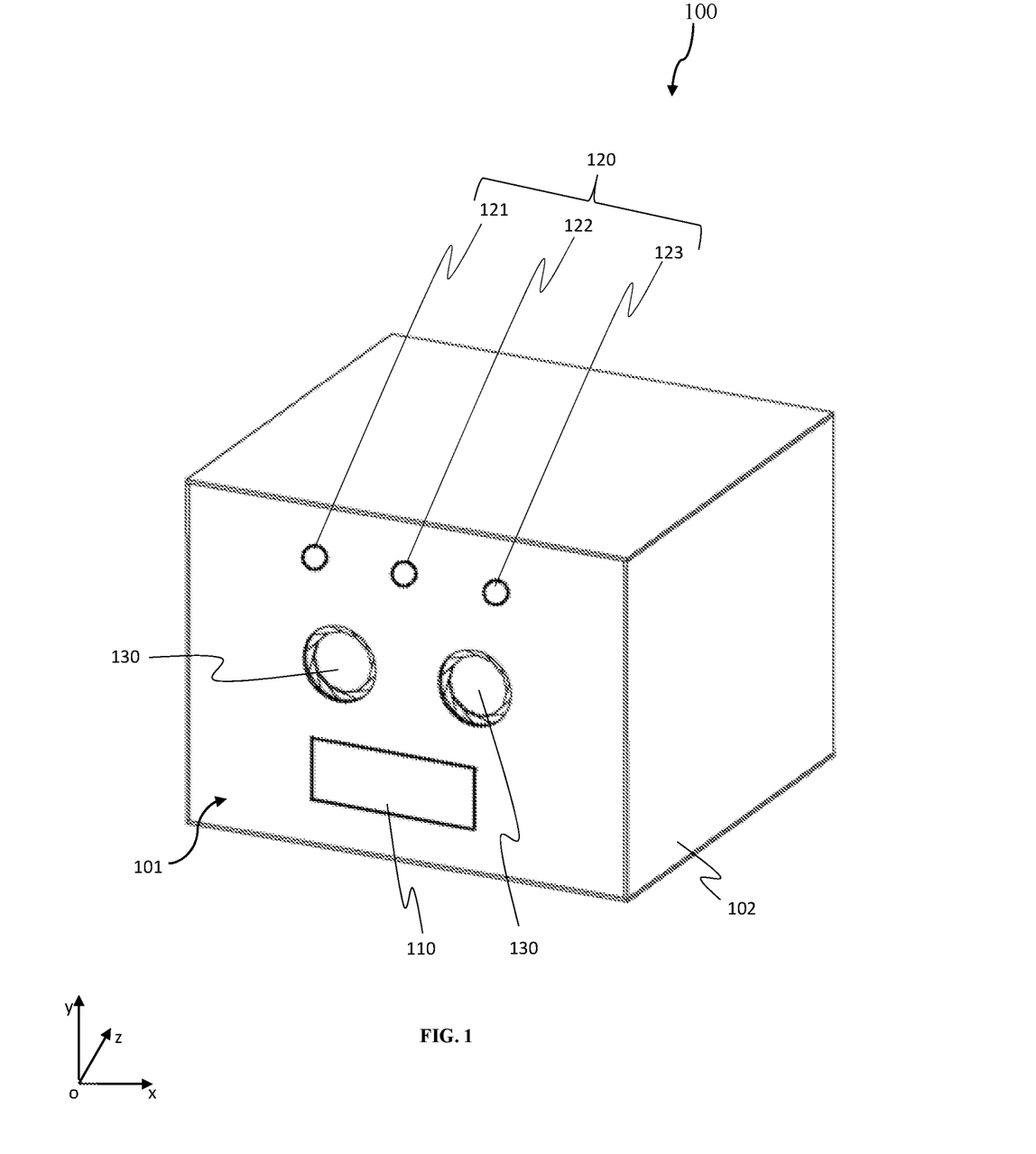
FIG. 1 illustrating the exterior of hand washing, disinfection and automatic massage machine seen from the front.

With reference to FIG. 1, the exterior of the hand washing, disinfection and automatic massage machine 100 seen from the front 101 in accordance with the invention. The hand washing, disinfection and automatic massage machine 100 is housed in case 102, wherein an LDC touch screen 110, signal LEDs 120 and holes 130 are located on the front side of case 102. The LCD touch screen 110 is used to display warnings, reminders, instructions on hand washing steps and washing progress, settings, etc. during user cleaning and disinfection of hands. The signal LEDs 120 are used to indicate the operating status of the hand washing, disinfection and automatic massage machine 100.

As shown in FIG. 1, the signal LEDs 120 include green light 121, yellow 122 and red light 123 and controlled by the control (not shown); wherein, the green light 121 shows the status of the hand washing, disinfection and automatic massage machine 100 ready to use. The yellow light 122 indicates hand washing machine 100 is in the hand hygiene process. The red light 123 indicates the machine having a problem, troubleshooting or reporting an error.

Figure 2A:
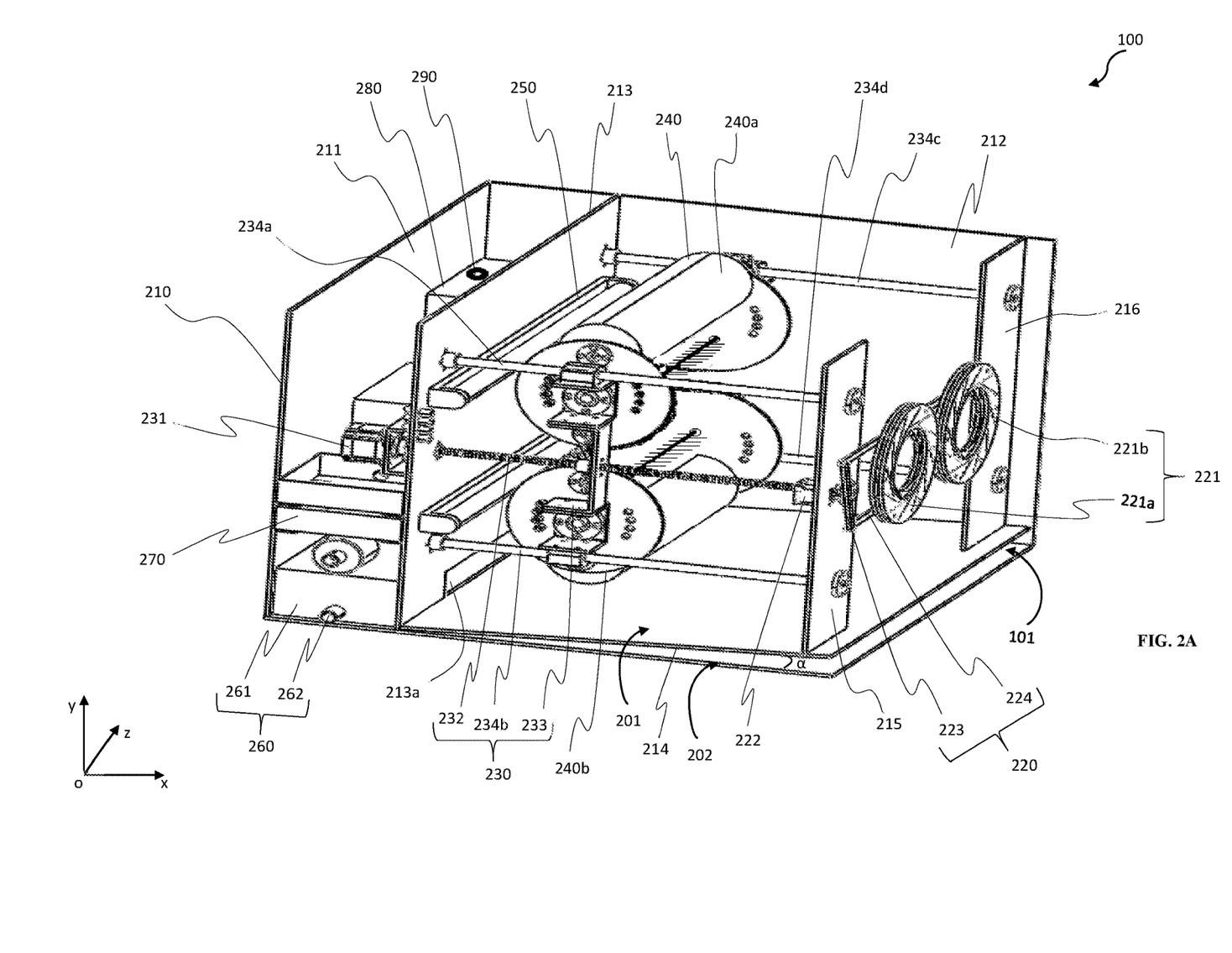
FIG. 2A illustrating the internal structure of hand washing, disinfection and automatic massage machine seen from the left side.

Referring to FIG. 2A, the internal structure of the hand washing machine 100 seen from the left side 201, a support frame 210, a wrist lock controller 220, a movement controller 230, a washing and disinfection compartment 240, at least one UV lamp 250, a wastewater treatment compartment 260, a water pump and air blower compartment 270, an energy source 280, and a controller 290.

As shown in FIG. 2A, the support frame 210 mechanically connect the wrist lock controller 220, the movement controller 230, the washing and disinfection compartment 240, the UV lamps 250, the wastewater treatment compartment 260, the water pump and air blower compartment 270, the energy source 280 and the controller 290. The wrist lock controller 220 is used to open/close to prevent water, soap solution, air and disinfectant solution from going out the hand washing machine 100 during hand hygiene. The movement controller 230 controls and directs the movement of the washing and disinfection compartment 240. The washing and disinfection compartment 240 is used for washing, disinfecting and massaging hands. The UV lamps 250 are responsible for the disinfection of the inside of the hand washing, disinfection and automatic massage machine 100. The wastewater treatment component 260 keeps the wastewater inside the hand washing, disinfection and automatic massage machine 100. The water pump and air blower compartment 270 supplies clean water, soap solution, disinfectant solution and air to the washing and disinfection compartment 240 for hand hygiene. The energy source 280 supplies power to LCD touch screen 110, signal LEDs 120, wrist lock controller 220, movement controller 230, washing and disinfection compartment 240, UV lamps 250, water pump and air blower compartment 270, controller 290 by electrical connections; wherein, the energy source 280 includes direct power source, carbon battery, alkaline battery, silver oxide battery, lithium battery, lead oxide battery, solar battery, etc. The controller 290 controls the LCD touch screen 110, signal LEDs 120, wrist lock controller 220, movement controller 230, washing and disinfection compartment 240, UV lamps 250, and water pump and air blower compartment 270; the controller 290 is programmed with software to control hand hygiene operations of the hand washing, disinfection and automatic massage machine 100 to perform the method of hand hygiene.

As shown in FIG. 2A, storage chamber 211, washing chamber 212, partition 213, bottom liner 214, left support plate 215, right support plate 216, are connected by support frame 210. The chamber 211 is housed with the wastewater treatment compartment 260, the water pump and air blower compartment 270, the energy source 280. The washing chamber 212 is installed with the wrist lock controller 220, the washing and disinfection compartment 240, the UV lamps 250. The partition 213 is used to prevent water, soap solution and disinfectant solution from the washing chamber 212 into the storage chamber 211 during hand hygiene; on partition 213, where it is in contact with the bottom liner 214 with a drainage hole 213a used to bring dirty water from the washing chamber 212 to the wastewater treatment compartment 260. The bottom liner 214 which is tilted from the bottom side 202 of the support frame 210 at an angle of 5° to 45° direction from front 101 to the partition 213, is used to bring dirty water inside the washing chamber 212 to the wastewater treatment compartment 260 through the drainage hole 213a. The left and right support plate 215, 216 are placed parallel and evenly spaced with the partition 213, and the movable controller 230 forming a rack for the washing and disinfection compartment 240.

As shown in FIG. 2A, the wrist lock controller 220 includes a wrist lock mechanism 221, a first motor 222, a rotary bar 223, and thrust levers 224. The wrist lock mechanism 221 is installed on the case 102 on the front 101 of the hand washing, disinfection and automatic massage machine 100, includes a left and right wrist lock mechanism 221a and 221b placed parallel to each other at the same time centrifuged with the holes 130.

Figures 2B, 2C, 2D:
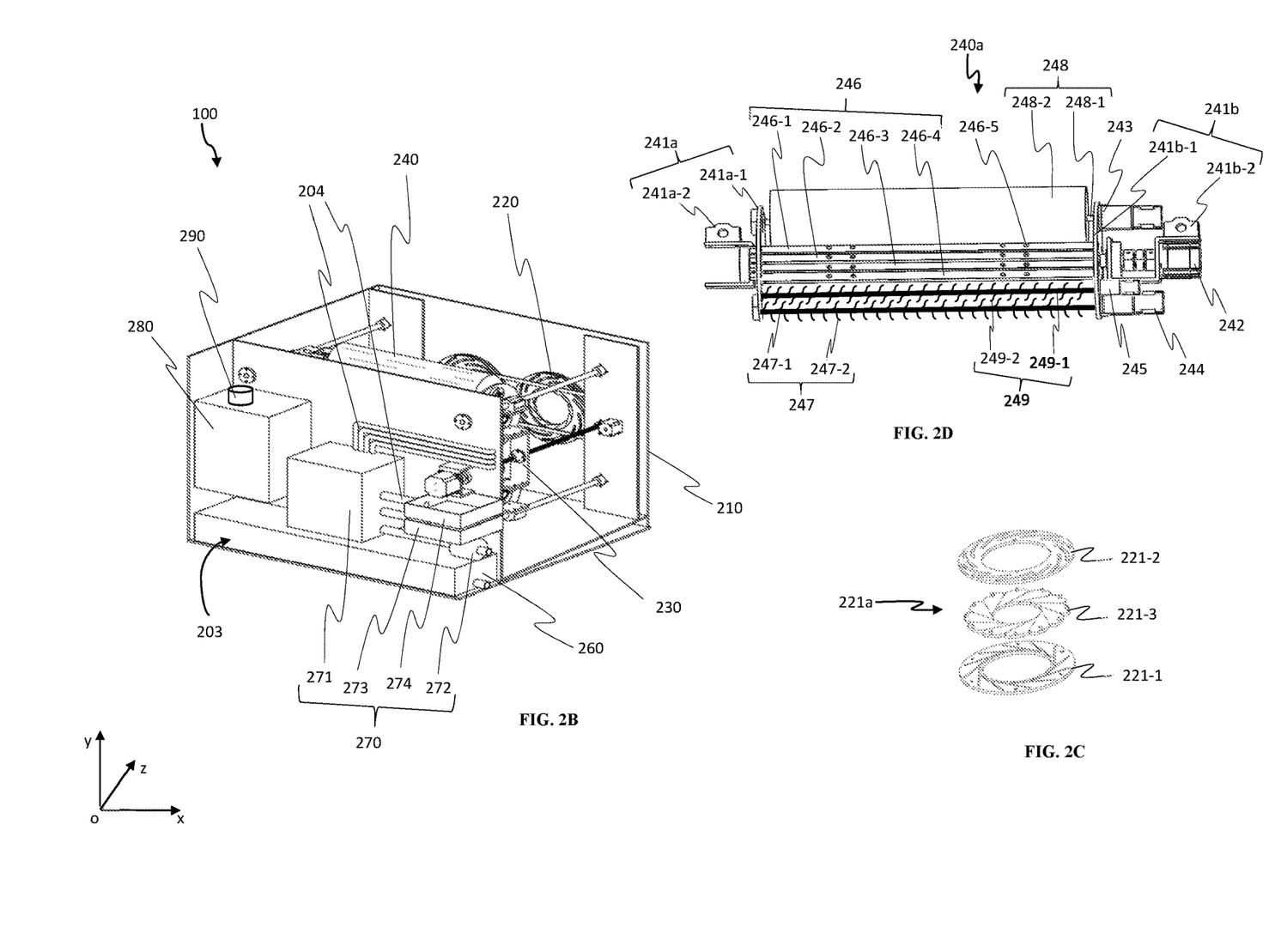
FIG. 2B illustrating the internal structure of hand washing, disinfection and automatic massage machine seen from the back.
FIG. 2C illustrating structure of the wrists lock mechanism.
FIG. 2D illustrating structure of the washing and disinfection equipment of the washing and disinfection compartment.

Referring to FIG. 2C, shows left wrist lock mechanism 221a includes a fixed plate 221-1, a movable plate 221-2, and movable blades 221-3 located between the fixed plate 221-1 and the movable plate 221-2. The fixed plate 221-1 and the movable plate 221-2 are in forms of a hollow, flat circle, have the same size and are mechanically connected together to create a space for the user to put their hands in the washing chamber 212 of the support frame 210 for cleaning; wherein the fixed plate 221-1 is fixed to the case 102 of the hand washing, disinfection and automatic massage machine 100. The movable blades 221-3 are mechanically connected to the movable plate 221-2 and are rounded in one direction. The movable plate 221-2 is mechanically connected with the thrust levers 224 and can be rotated so that the movable blades 221-3 perform the open/close of the left wrist lock mechanism 221a, thereby helping to close/open the holes 130 on the hand washing, disinfection and automatic massage machine 100. It should be noted that the structure of the left wrist lock mechanism 221a and the right wrist lock mechanism 221b is the same.

Returning to FIG. 2A, the first motor 222 is permanently mounted on the left support plate 215, electrically connected to the energy source 280 and mechanically connected to a rotary bar 223, used to control the wrist lock mechanism 221 adopts rotary bar 223 and the thrust levers 224. The thrust levers 224 is used to connect the two ends of the rotary bar 223 with the movable plates 221-2 of the wrist lock mechanism 221. When in operation, the first motor 222 drives to the rotary bar 223 and the thrust levers 224, allowing the movable plates 221-2 to rotate, causing the movable blades 221-3 to open/retract, thereby implementing the gap opening/closing function on the wrist lock mechanism 221.

As shown in FIG. 2A, the movement controller 230 includes a second motor 231, rotating shaft 232, a batten plate 233, and guide shafts 234. The second motor 231 is fixed on the partition 213 and inside the storage chamber 211, electrically connected to the energy source 280, driven to the rotating shaft 232 makes the washing and disinfection compartment 240 moves in a linear direction towards the X direction of rotating shaft 232 and guide shafts 234 in operation. The batten plate 233 is located on the rotating shaft 232 and connects and drives the washing and disinfection compartment 240. The guide shafts 234 includes a first guide shaft 234a, a second guide shaft 234b, a third guide shaft 234c, and a fourth guide shaft 234d; the one end guide shafts 234a and 234b mechanically connected to the left support plate 215, and the other end mechanically connected to the partition 213; similarly one end of guide shafts 234c and 234d mechanically connected to right support plate 216, and the other end mechanically connected to the partition 213; the guide shafts 234a, 234b, 234c, 234d are parallel to each other to support and guide the movement of the washing and disinfection compartment 240. The rotating shaft 232 located between guide shafts 234a, 234b; one end of rotating shaft 232 mechanically connected to the second motor 231, the other end fixed to the left support plate 215.

As shown in FIG. 2A, the washing and disinfection compartment 240 includes an upper washing and disinfection equipment 240a and a lower washing and disinfection equipment 240b are located in parallel to the Y direction and connected to each other via batten plate 233, creates a gap opposite to wrist lock mechanism 221 in the X direction for handing cleaning; the upper washing and disinfection equipment 240a has one end connected to the first guide shaft 234a and the batten plate 233, the other end to the third guide shaft 234c; the lower washing and disinfection equipment 240b has one end connected to the second guide shaft 234b and batten plate 233, the other end connected to the fourth guide shaft 234d.

Referring to FIG. 2D, a depiction in detail of the structure of the upper washing and disinfection equipment 240a of the washing and disinfection compartment 240. The upper washing and disinfection equipment 240a includes a left connector 241a, a right connector 241b, a third motor 242, a fourth motor 243, a fifth motor 244, a sixth motor 245, a duct cluster 246, a brush cluster 247, a wiper cluster 248, and a massage cluster 249. The left connector 241a includes a left circular disc 241a-1, and a first fixed plate 241a-2, for connection to the first guide shaft 234a and the batten plate 233. The right connector 241b includes a right circular disc 241b-1 and a second fixed plate 241b-2, for the connection to the third guide shaft 234c. The circular discs 241a-1 and 241b-1 form the support frame and are mechanically connected to the duct cluster 246, the brush cluster 247, the wiper cluster 248 and the massage cluster 249.

The third motor 242 connected to the right circular disc 241b-1, to control the upper washing and disinfection equipment 240a, thereby helping to adjust the duct cluster 246, the brush cluster 247, the wiper cluster 248 and the massage cluster 249 to the location to be cleaned. The fourth motor 243 is connected to the right circular disc 241b-1, which is used to drive the wiper cluster 248. The fifth motor 244 is connected to the right circular disc 241b-1, which is used to drive the brush cluster 247. The sixth motor 245 is connected to the right circular disc 241b-1, which is used to drive the massage cluster 249. All motors 242, 243, 244, 245 are powered by energy power 280.

The duct cluster 246 includes a clean water pipe 246-1, a soap pipe 246-2, an air pipe 246-3, and a disinfectant solution pipe 246-4. On each pipeline of the duct cluster 246 a plurality of nozzles 246-5 are arranged to spray soap solution, clean water, air, and disinfectant solution on the users' hands. The brush cluster 247 includes a brush cluster drive shaft 247-1, having multiple plastic fibers 247-2 mounted thereon, used to scrub the dirt on the hand. The wiper cluster 248 includes a wiper cluster drive shaft 248-1, and a wiper 248-2 in a cylindrical shape, made of water-repellent material, to dry hands. The massage cluster 249 includes a massage cluster drive shaft 249-1, having a plurality of silicon fibers 249-2 mounted thereon, to massage hands after hand hygiene.

It should be noted that the construction of the upper washing and disinfecting equipment 240a and the lower washing and disinfection equipment 240b is the same. The combination of the washing and disinfection equipments 240a and 240b keeps hands clean on both the back of the hand and the palm.

As shown in FIG. 2A, the UV lamp 250 installed on the partition 213 on the side of the washing chamber 212, will operate for a specified period of time after the user has finished hand hygiene and the wrist lock mechanism 221 has been completely closed; at least one UV lamp 250 disinfects the internal components of the wash chamber 212.

As shown in FIG. 2A, a wastewater treatment compartment 260 includes a wastewater treatment box 261 and an outlet pipe 262. The wastewater treatment box 261 is mechanically connected to the partition 213 and connected to the washing chamber 212 via drainage hole 213a on the bottom of partition 213. The outlet pipe 262 is to remove the wastewater from the wastewater treatment box 261 out of the hand washing, disinfection and automatic massage machine 100.

As shown in FIG. 2A, the controller 290 is a −16 or −32 bit Programmable Logic Controller (PLC), a Supervisory Control and Data Acquisition (SCADA), or any other type of programmable logic array (PLA) consisting of a memory chip and integrated circuits for control logic, monitoring, and communicating. The controller 290 directs the programmable logic controller (PLC) and/or to execute control instructions, communicate with others, carry out logic and arithmetic operations, and perform internal diagnostics. The controller 290 runs memory routines, constantly checking the PLC to avoid programming errors and ensure the memory is undamaged. Memory provides permanent storage to the operating system for database used by controller 290. Five programming languages are used in controller 290 and PLC. They are defined by the international standard IEC 61131. Ladder logic is one of the most commonly used PLC languages. Another programming language is function block diagram (FBD). It describes functions between input and output variables. The function, represented by blocks, connects input and output variables. FBD is useful in depicting algorithms and logic from interconnected controls systems. Structured Text (ST) is a high-level language that uses sentence commands. In ST, programmers can use "if/then/else", "SART" or "repeat/until" statements to create programs. Instruction list (IL) is a low-level language with functions and variables defined by a simple list. Program control is done by jump instructions and sub-routines with optional parameters. Sequential Function Chart (SFC) language is a method of programming complex control systems. It builds the basic blocks used to execute subroutines. Program files can be written in different programming languages. The SFC breaks down large and complex programming tasks into smaller and more manageable tasks. In the various variants of the invention, the controller 290 includes, but is not limited to, desktops, notebook computers, programmable logic controller (PLC), monitoring and receiver controller data acquisition (SCADA) or any other type of microprocessor or logic array programmer chip.

Referring to FIG. 2B, the internal structure of hand washing, disinfection and automatic massage machine 100 seen from the back side 203. The water pump and air blower compartment 270 includes a pump 271, a water filter 272, a soap compartment 273, and a disinfectant solution compartment 274. The pump 271 fixed on the partition 213, mechanically connected to water filter 272, the liquid hand soap compartment 273 and the disinfectant solution compartment 274 through first pipes 204. The pump 271 that receives energy from an energy source 280, pumps the liquid hand soap, clean water, air, and disinfectant solution to the corresponding pipes of duct cluster 246 of the washing and disinfection compartment 240 through the first pipe 204. The water filter 272 is electrically connected to the energy source 280, with one end placed in contact with the outside of the hand washing, disinfection and automatic massage machine 100 to obtain clean water outside the pump 271. The soap compartment 273 and disinfectant solution 274 mechanically connected to the partition 213.

The clean water pipe 246-1, soap pipe 246-2, air pipe 246-3, disinfectant solution pipe 246-4, and first pipe 204 has circular shape, hollow inside, facilitates solvent flow between the hand washing, disinfection and automatic massage machine 100.

Figure 3:
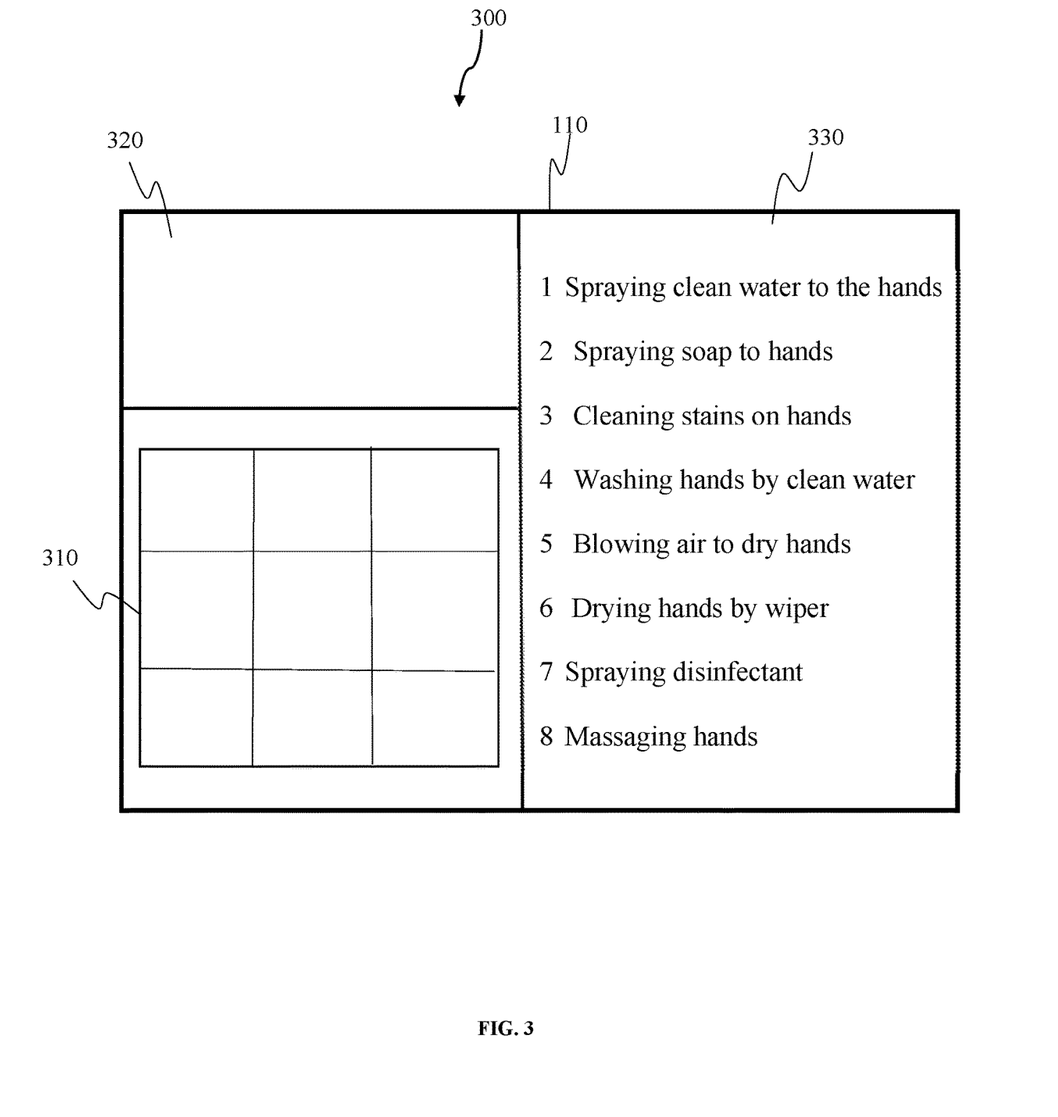
FIG. 3 shows an interface of the LCD touch screen interface of hand washing and disinfection and automatic massage machine.

Referring to FIG. 3, a shows an interface 300 of the LCD touch screen 110 of hand washing and disinfection and automatic massage machine 100 according to the exemplary embodiment of the invention. The LCD touch screen 110 is connected and receives information from the controller 290. During the process of the hand washing machine 100, the interface 300 of the LCD touch screen 110 of will display settings, progress and problems of the hand washing, disinfection and automatic massage machine 100. Therefore users can choose settings for time, speed, number of repetitions, etc. of cleaning process and track hand washing progress through interface 300 of the LCD touch screen 110. Moreover, problems can occur inside the hand washing, disinfection and automatic massage machine 100 such as hand partly washed, hand position error, disinfection, out of hand soap and disinfectant solution, the hand washing, disinfection and automatic massage machine 100 out of order etc. also displayed on the interface 300 of the LCD touch screen 110.

The interface 300 of the LCD touch screen 110 comprises a setting keys 310, an information display section 320, and a table of progress for hand hygiene 330. The setting keys 310 allow users to select and set the operation modes of the hand washing machine 100. The information display section 320 shows errors of the hand washing machine 100 as well as the errors users make during hand washing and disinfection such as not getting their hands in the right place, etc. also displays instructions for setting and use for the hand washing, disinfection and automatic massage machine 100. The table of progress for hand hygiene 330 shows the steps of hand washing performed by the hand washing, disinfection and automatic massage machine 100 and shows the user's washing process at the step of the hand washing and disinfection process.

The hand washing, disinfection and automatic massage machine 100 also includes an additional sensor component (not shown) including distance sensors, to collect information of the user's hand distance and position and send it to the controller 290, the sensor component is an internet of things (IoT) device.

Figure 4:
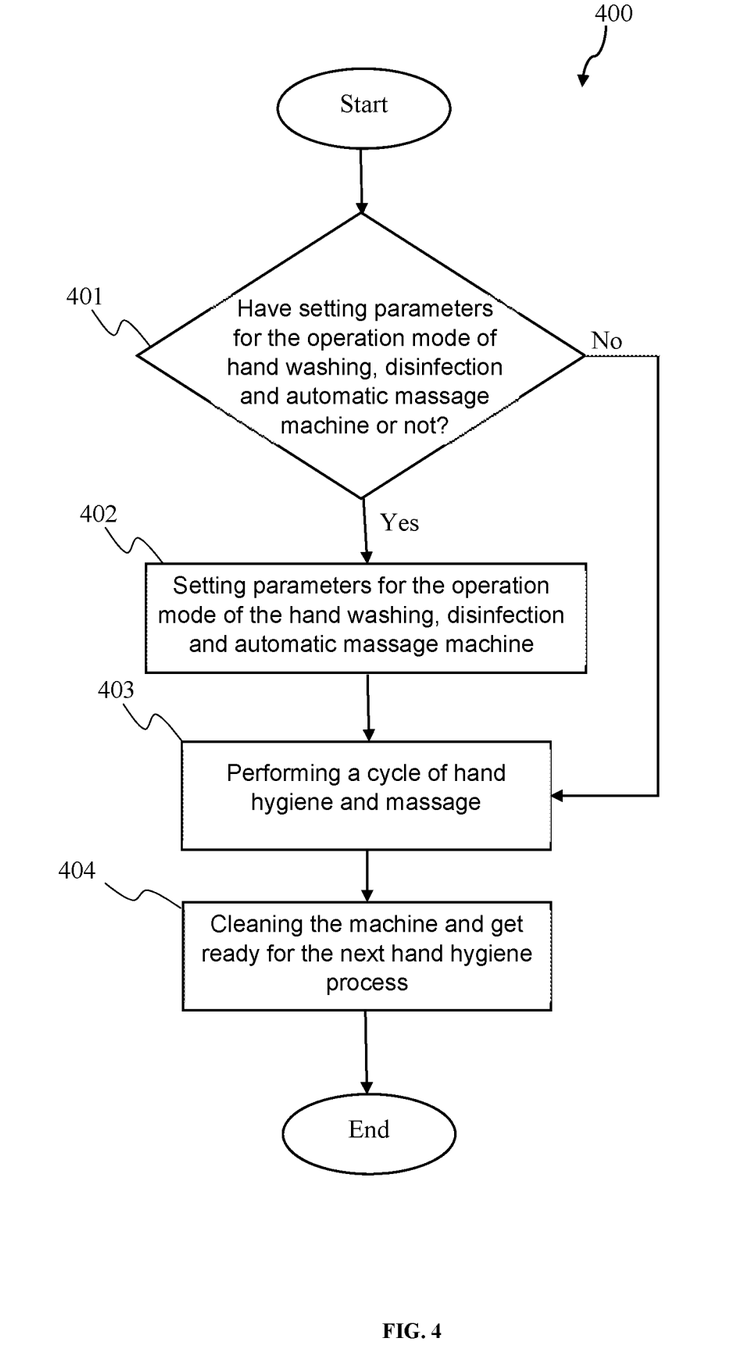
FIG. 4 illustrating flowchart of a method of operating a hand washing and disinfection and automatic massage machine.

Referring to FIG. 4, a flowchart illustrating a method 400 of operating a hand washing, disinfecting and massage automatic machine 100 according to the invention. The controller 290 is programmed with software to control hand hygiene activities of the hand washing, disinfection and automatic massage machine 100 to perform method 400.

The method 400 begins with step 401; selection of setting parameters for the operation mode of hand washing, disinfection and automatic massage machine 100. When the green light 121 of the signal LEDs 120 turn on indicates the hand washing, disinfection and automatic massage machine 100 is ready for handing hygiene. To begin, the users have the option whether to change the operation mode of the hand washing, disinfection and automatic massage machine 100 or not. If users do not want to change the operating modes then, go to step 403; and vice versa if the users do want to change the operation mode (pre-programmed for the hand washing, disinfection and automatic massage machine 100), go to step 402.

In step 402, setting parameters for operation modes of the hand washing, disinfection and automatic massage machine 100. The hand washing, disinfection and automatic massage machine 100 are programmed with default parameters of execution time and number of repetitions at each step of the hand hygiene cycle, movement speed of the washing and disinfection compartment 240, etc. These parameters are the minimum parameters that have been researched and proven to be effective for hand hygiene performed by the hand washing, disinfection and automatic massage machine 100. Users setting parameters for the controller 290 operation modes through the setting keys 310 on the interface 300 of the LCD touch screen 110 to make the parameter value adjustment execution time and number of repetitions at each step of the hand hygiene cycle, movement speed of the washing and disinfection compartment 240, etc. However, the parameters set by the user shall not be less than the values of the pre-programmed parameters of the hand washing, disinfection and automatic massage machine 100.

In step 403, users put their hands in the washing chamber 212 of the hand washing, disinfection and automatic massage machine 100 and perform a cycle of hand hygiene and massage. Specifically, the first motor 222 transmits motion to the rotary bar 223 and the thrust levers 224, the movable plates 221-2 rotate makes the movable blades 221-3 record, creates the largest gap on the wrist lock mechanisms 221 for users to easily put their hands into the washing chamber 212 of the hand washing, disinfection and automatic massage machine 100. If the user's hand is not properly positioned for cleaning, an error message will be displayed in the information display section 320 in the interface 300 of the LCD touch screen 110. After the user's hands are in the correct position for cleaning, the first motor 222 will control the wrist lock mechanisms 221 causing the movable blades 221-3 slowly radiate until they touch the user's hand stop. At this time, the yellow light 122 of the signal LEDs 120 will light up to indicate that the hand washing, disinfection and automatic massage machine 100 is performing the hand hygiene process. Next, the washing and disinfection compartment 240 will perform the cycle of hand hygiene and massage.

In step 404, cleaning the device and getting ready for the next hand hygiene process. At the end of the step 403, the first motor 222 will control the wrist locking mechanisms 221 so that the movable blades 221-3 record, creating the largest gap on the wrist lock mechanisms 221 for the user to easily reach out of the washing chamber 212. Then, the first engine 222 controls the wrist lock mechanisms 221 causing the movable blades 221-3 to radiate completely, helping to close the gaps on the wrist lock mechanisms 221. Next, the motors 243, 244 and 245 will spin at high speed to cause water to splash from the wiper cluster 248, the brush cluster 247, and the massage cluster 249 by centrifugal force. Finally, the UV lamps 250 are turned on at a preset time by the controller 290 to disinfect inside of the washing chamber 212. At the end of the hand hygiene process, the controller 290 turns off the UV lamps 250, and the green light 121 of the signal LEDs 120 lights up to indicate the hand washing, disinfection and automatic massage machine 100 is ready for use by the next user. For the case of a user performing step 402, the controller 290 adjusts the hand washing, disinfection and automatic massage machine 100 to the default programmed operation mode.

Figure 5:
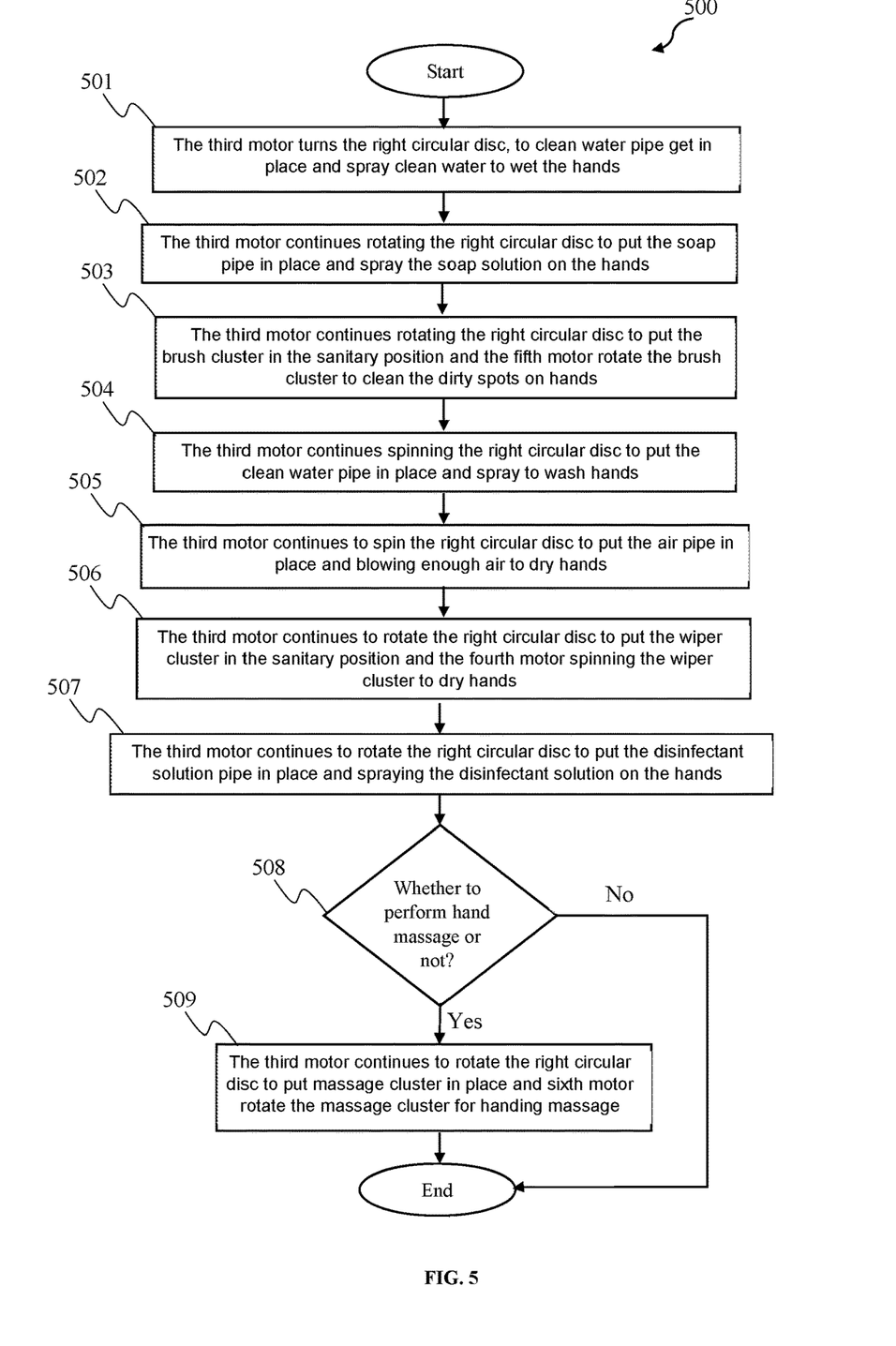
FIG. 5 illustrating flowchart of a cycle of hand hygiene and massage.

Referring to FIG. 5, a flowchart illustrating a cycle of hand hygiene and massage ("cycle 500") of method 400 performed by the washing and disinfection compartment 240. The cycle 500 begins with step 501, the second motor 231 will control the washing and disinfection compartment 240 translational motion on the rotating shaft 232, and the third motor 242 turns the right circular disc 241*b*-1, help clean water pipe 246-1 get in place and spray clean water to wet the hands evenly.

In step 502, the third motor 242 continues spinning the right circular disc 241*b*-1 to put the soap pipe 246-2 get in place and spray the liquid soap on the hands; while the second motor 231 controls the washing and disinfection compartment 240 translational motion on the rotating shaft 232, allowing the soap solution to be sprayed evenly.

In step 503, the third motor 242 continues to rotate the right circular disc 241*b*-1 to put the brush cluster 247 in the sanitary position and the fifth motor 244 will rotate the brush cluster 247 to clean the whole spot dirty on hands; at the same time the second motor 231 controls the washing and disinfection compartment 240 translational motion on the rotating shaft 232 so that the brush cluster 247 can clean the whole hand.

In step 504, the third motor 242 continues to spin the right circular disc 241*b*-1 to put the clean water pipe 246-1 get in place and spray clean water to wash hands; while the second motor 231 controls the washing and disinfection compartment 240 translational motion on the rotating shaft 232 to allow clean water to be sprayed evenly.

In step 505, the third motor 242 continued to spin the right circular disc 241*b*-1 to put the air pipe 246-3 in place and blow enough air to dry the hands; while the second motor 231 controls the washing and disinfection compartment 240 in translational motion on the rotating shaft 232 to help dry evenly.

In step 506, the third motor 242 continues to rotate the right circular disc 241*b*-1 to put the wiper cluster 248 in the sanitary position and the fourth motor 243 will spinning the wiper cluster 248 to dry hands; at the same time the second motor 231 controls the washing and disinfection compartment 240 translational motion on the rotating shaft 232 so that the wiper cluster 248 can dry evenly.

In step 507, the third motor 242 continues to rotate the right circular disc 241*b*-1 to put the disinfectant solution pipe 246-4 get in place and spray the disinfectant solution on the hands; while the second motor 231 controls the washing and disinfection compartment 240 translational motion on the rotating shaft 232 to allow the disinfectant to be sprayed evenly.

In step 508, consider whether washing and disinfection compartment 240 performs hand massage; if "YES", proceed to step 509; otherwise terminate cycle 500.

In step 509, the third motor 242 continues to rotate the right circular disc 241*b*-1 to put massage cluster 249 in place and the sixth motor 245 will rotate massage cluster 249 for handing massage; while the second motor 231 controls the washing and disinfection compartment 240 moves forward on the rotating shaft 232 so that the massage cluster 249 can massage the whole hand.

Each step of the above hand massage and cleaning cycle is performed for a period, the number of repetitions and the speed of the device is pre-programmed or set in step 402.

Implementations of hand washing, disinfection and automatic massage machine 100 and method 400 disclosed above achieve the following objectives:

The hand washing, disinfection and automatic massage machine 100 with automatic operation, performing the process of cleaning and disinfecting hands according to the steps given by the Ministry of Health to help ensure hand hygiene before eating, before and after contact with a sick person, when exposed to a polluted environment, before entering a public place or entering a home, etc. At the same time, this machine also has a massage function to help create comfort for the hands.

The invention also launched a hand washing, disinfection and automatic massage machine 100 have simple structure, low cost, easy installation and operation, suitable for use everywhere, all objects used and provide a high degree of infection prevention.

The disclosed flowchart and block diagrams illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two consecutive blocks shown may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent those of ordinary skill in the art without departing from the scope and spirit of the invention.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

These claims should be construed to maintain the proper protection for the invention first described. It will be understood that those skilled in the art, both now and in the future, may make various improvements and enhancements which fall within the scope of the claims which follow. These claims should be construed to maintain the proper protection for the invention first described.

DESCRIPTION OF NUMERALS

100 Hand washing, disinfection and automatic massage machine
101 Front
102 Case
110 LCD touch screen
120 Signal LEDs
121 Green light
122 Yellow light
123 Red light
130 Holes
201 Left side
202 Bottom side
203 Back side
204 First pipe
210 Support frame
211 Storage chamber
212 Washing chamber
213 Partition
213a Drainage hole
214 Bottom liner
215 Left support plate
216 Right support plate
220 Wrist lock controller
221 Wrist lock mechanism
221a Left wrist lock mechanism
221b Right wrist lock mechanism
221-1 Fixed plate
221-2 Movable plate
221-3 Movable blades
222 First motor
223 Rotary bar
224 Thrust lever
230 Movement controller
231 Second motor
232 Rotating shaft
233 Batten plate
234 Guide shafts
234a First guide shaft
234b Second guide shaft
234c Third guide shaft
234d Fourth guide shaft
240 Washing and disinfection compartment
240a Upper washing and disinfection equipment
240b Lower washing and disinfection equipment
241a Left connector
241a-1 Left circular disc
241a-2 First fixed plate
241b Right connector
241b-1 Right circular disc
241b-2 Second fixed plate
242 Third motor
243 Fourth motor
244 Fifth motor
245 Sixth motor
246 Duct cluster
246-1 Clean water pipe
246-2 Soap pipe
246-3 Air pipe
246-4 Disinfectant solution pipe
246-5 Nozzles
247 Brush cluster
247-1 Brush cluster drive shaft
247-2 Plastic fiber
248 Wiper cluster
248-1 Wiper cluster drive shaft
248-2 Wiper
249 Massage cluster
249-1 Massage cluster drive shaft
249-2 Silicone fiber
250 UV lamp
260 Wastewater treatment compartment
261 Wastewater treatment box
262 Outlet pipe
270 Water pump and air blower compartment
271 Pump
272 Water filter
273 Soap compartment
274 Disinfectant solution compartment
280 Energy source
290 Controller
300 Interface
310 Setting keys
320 Information display section
330 Table of progress for hand hygiene

What is claimed is:

1. A hand washing, disinfection and automatic massage machine, comprising:
a Liquid Crystal Display (LCD) touch screen, signal Light-Emitting Diodes (LEDs), a support frame, a wrist lock controller, a movement controller, a washing and disinfection compartment, Ultraviolet (UV) lamps, a wastewater treatment compartment, a water pump and air blower compartment, an energy source, and a controller;
wherein the hand washing, disinfection and automatic massage machine is housed in a case;
wherein the LCD touch screen and the signal LEDs are installed in front of the case;

wherein the LCD touch screen displays warnings, reminders, instructions on hand washing steps and washing progress, and settings during user cleaning and disinfection of hands;
wherein the signal LEDs indicates the operating status of the hand washing, disinfection and automatic massage machine;
wherein the support frame is mechanically connected to the wrist lock controller, the movement controller, the washing and disinfection compartment, the UV lamps, the wastewater treatment compartment, the water pump and air blower compartment, the energy source, and the controller;
wherein the wrist lock controller comprises a wrist lock mechanism, a first motor, a rotary bar, and thrust levers;
wherein the wrist lock mechanism comprises a movable plate mechanically connected to the thrust levers and configured to rotate so movable blades open and close to prevent water, soap solution, air and disinfectant solution from going out of the hand washing, disinfection and automatic massage machine during hand hygiene;
wherein the movement controller controls and directs the movement of the washing and disinfection compartment;
wherein the washing and disinfection compartment is used for washing, disinfecting and massaging hands;
wherein the UV lamps are responsible for disinfecting of the inside of the hand washing, disinfection and automatic massage machine;
wherein the wastewater treatment compartment is configured to keep wastewater inside the hand washing, disinfection and automatic massage machine;
wherein the water pump and air blower compartment supplies clean water, soap, disinfectant solution and air to the washing and disinfection compartment for hand hygiene;
wherein the controller is programmed with software to control hand hygiene operations of the hand washing, disinfection and automatic massage machine.

2. The hand washing, disinfection and automatic massage machine according to claim 1, further comprising a pair of holes for inserting hands inside the machine.

3. The hand washing, disinfection and automatic massage machine according to claim 1, wherein the signal LEDs comprises a green light, a yellow light, and a red light;
wherein the green light indicates the machine is ready for use;
wherein the yellow light indicates the machine is performing the hand hygiene process; and
wherein the red light indicates the machine is having problems with the operating process.

4. The hand washing, disinfection and automatic massage machine according to claim 1, further comprising a storage chamber, a washing chamber, a partition, a bottom liner, a left support plate, and a right support plate;
wherein the partition is in contact with the bottom liner via a drainage hole to discharge dirty water from the washing chamber to the wastewater treatment compartment;
wherein the bottom liner is tilted from the bottom side of the support frame at an angle of 5° to 45°, in order to discharge dirty water inside the washing chamber to the wastewater treatment compartment through the drainage hole;
wherein the left support plate and the right support plate are placed parallel and spaced apart with the partition.

5. The hand washing, disinfection and automatic massage machine according to claim 1, wherein the wrist lock mechanism comprises a left wrist lock mechanism, and a right wrist lock mechanism paralleled to each other on the front side of the case;
wherein the left wrist lock mechanism and the right wrist lock mechanism each comprise a fixed plate, the movable plate, and the movable blades located between the fixed plate and the movable plate; the movable blades are round in one direction;
wherein the fixed plate and the movable plate are the same size and in the form of a hollow, flat circle and mechanically connected together and to the support frame;
wherein the first motor is mounted on the left support plate, electrically connected to the energy source and mechanically connected to the rotary bar, to control the wrist lock mechanism;
wherein the thrust levers connect the two ends of the rotary bar with the movable plates of the wrist lock mechanisms.

6. The hand washing, disinfection and automatic massage machine according to claim 1, wherein the movement controller comprises a second motor, a rotating shaft, a batten plate, and guide shafts;
wherein the second motor is fixed on a partition on the side of the storage chamber, electrically connected to the energy source, driven to the rotating shaft which makes the washing and disinfection compartment translationally move according to the orientation of the rotating shaft and guide shafts;
wherein the batten plate is located on the rotating shaft, to drive the washing and disinfection compartment;
wherein the guide shafts comprises a first guide shaft, a second guide shaft, a third guide shaft, and a fourth guide shaft; one end of the first guide shaft and the second guide shaft is mechanically connected to the left support plate, the other end mechanically connected to the partition; one end of the third guide shaft and the fourth guide shaft is mechanically connected to the right support plate, the other end mechanically connected to the partition;
wherein the guide shafts are placed parallel to each other, to support and guide the movement of the washing and disinfection compartment;
wherein the rotating shaft is located between the first guide shaft and the second guide shaft; one end of rotating shaft is mechanically connected to the second motor, and the other end fixed to the left support plate.

7. The hand washing, disinfection and automatic massage machine according to claim 1, wherein the washing and disinfection compartment comprising an upper washing and disinfection equipment, and a lower washing and disinfection equipment connected to each other in parallel via a batten plate;
wherein one end of the upper washing and disinfection equipment is connected to the first guide shaft and the batten plate, the other end is connected to the third guide shaft; one end of the lower washing and disinfection equipment is connected to the second guide shaft and the batten plate, the other end connected to the fourth guide shaft;
wherein each of the upper washing and disinfecting equipment and the lower washing and disinfection equipment comprises a left connector, a right connector, a third motor, a fourth motor, a fifth motor, a sixth motor, a duct cluster, a brush cluster, a wiper cluster, and a massage cluster;

wherein the left connector comprises a left circular disc, and a first fixed plate, for connection to the first guide shaft and the batten plate;

wherein the right connector comprises a right circular disc and a second fixed plate, for the connection to the third guide shaft;

wherein the left circular disc and the right circular disc form the support frame and are mechanically connected to the duct cluster, the brush cluster, the wiper cluster and the massage cluster;

wherein the third motor is connected to the right circular disc, to control the washing and disinfection equipment, and adjust the duct cluster, the brush cluster, the wiper cluster and the massage cluster;

wherein the fourth motor is connected to the right circular disc, which is used to drive the wiper cluster;

wherein the fifth motor is connected to the right circular disc, which is used to drive the brush cluster;

wherein the sixth motor is connected to the right circular disc, which is used to drive the massage cluster;

wherein the duct clusters comprises a clean water pipe, a soap pipe, an air pipe, and a disinfectant solution pipe; each of the pipes comprises a plurality of nozzles;

wherein the brush cluster comprises a brush cluster drive shaft, having multiple plastic fibers mounted thereon;

wherein the wiper cluster comprises a wiper cluster drive shaft, and a wiper;

wherein the massage cluster comprises a massage cluster drive shaft, having a plurality of silicon fibers mounted thereon.

8. The hand washing, disinfection and automatic massage machine according to claim 1, wherein the UV lamps are installed on a partition on the side of a washing chamber; operating for a predetermined period after the hand hygiene is complete and the wrist lock mechanism has been completely closed.

9. The hand washing, disinfection and automatic massage machine according to claim 1, wherein the wastewater treatment compartment comprising a wastewater treatment box and an outlet pipe;

wherein the wastewater treatment box is mechanically connected to a partition and to a washing chamber via a drainage hole on the partition;

wherein the outlet pipe is configured to discharge the wastewater from the wastewater treatment box.

10. The hand washing, disinfection and automatic massage machine according to claim 1, wherein the water pump and air blower compartment comprises a pump, a water filter, a soap compartment, and a disinfectant solution compartment;

wherein the pump is mechanically connected to the water filter, the soap compartment and the disinfectant solution compartment;

wherein one end of the water filter is located outside the case to obtain clean water.

11. The hand washing, disinfection and automatic massage machine according to claim 1, wherein the LCD touch screen comprises an interface having setting keys, an information display section, and a table of progress for hand hygiene.

12. A method of operating a hand washing, disinfection and automatic massage machine comprising a Liquid Crystal Display (LCD) touch screen, signal Light-Emitting Diodes (LEDs), a support frame, a wrist lock controller comprising a wrist lock mechanism, a first motor, a rotary bar, and thrust levers, the wrist lock mechanism comprising a fixed plate, a movable plate, and movable blades located between the fixed plate and the movable plate, the hand washing, disinfection and automatic massage machine further comprising a movement controller, a washing and disinfection compartment, Ultraviolet (UV lamps), a wastewater treatment compartment, a water pump and air blower compartment, an energy source, and a controller, said method including the following steps:

i) selecting setting parameters for the operation mode of said hand washing, disinfection and automatic massage machine; if a user wants to change the operation mode pre-programmed for the hand washing, disinfection and automatic massage machine follow step ii); otherwise perform step iii);

ii) setting parameters for the controller to control operation mode of the hand washing, disinfection and automatic massage machine through setting keys on the interface of the LCD touch screen; wherein the parameters set by the user shall not be less than the values of the pre-programmed parameters of the hand washing, disinfection and automatic massage machine;

iii) performing a cycle of hand hygiene and massage by the controller that transmits motion to the rotary bar and the thrust levers, to rotate the movable plates and the movable blades creating full openings on the wrist lock mechanisms for the user to insert their hands into the washing chamber; if the user's hands are in the correct position, the wrist lock mechanisms are driven by the first motor causing the movable blades to slowly radiate until they touch the user's hand, and the yellow light of the signal LEDs lights up to indicate that the hand washing, disinfection and automatic massage machine is performing the hand hygiene process;

wherein the washing and disinfection compartment performs the cycle of hand hygiene and massage;

if the user's hand is not properly positioned, an error message is displayed on the interface of the LCD touch screen;

iv) cleaning the machine and getting ready for the next hand hygiene process by controlling the wrist locking mechanisms so that the movable blades radiate completely to close the wrist lock mechanisms; next, spinning a fourth motor, a fifth motor and a sixth motor at high speed to cause water to splash from a wiper cluster, a brush cluster and a massage cluster; finally, turning the UV lamps on for a preset time to disinfect inside the washing chamber; at the end of the hand hygiene process, the UV lamps are off, and the green light of the signal LEDs lights up to indicate the hand washing, disinfection and automatic massage machine is ready for next hand hygiene;

wherein for the case of a user performing step ii), the controller adjusts the hand washing, disinfection and automatic massage machine to the default programmed operation mode.

13. The method of claim 12, further comprising wherein in step iii) the cycle of hand hygiene and massage is performed by the washing and disinfection compartment including the following steps:

a) spraying clean water to the hands by a second motor which makes the washing and disinfection compartment translationally move on the rotating shaft, and a third motor turns a right circular disc, to move a clean water pipe in place and spray clean water to wet the user's hands;

b) spraying soap to the user's hands by controlling the third motor continues rotating the right circular disc to put the soap pipe in place and spray the soap solution on the user's hands;
while the second motor controls the washing and disinfection compartment in translational motion on the rotating shaft;
c) cleaning stains on the user's hands by controlling the third motor to continue rotating the right circular disc to put the brush cluster in a sanitary position and the fifth motor rotates the brush cluster to clean dirty spots on the user's hands; at the same time the second motor controls the washing and disinfection compartment in translational motion on the rotating shaft so that the brush cluster can clean the user's entire hands;
d) washing the user's hands by controlling the third motor continues spinning the right circular disc to put the clean water pipe in place and spray to wash the user's hands; while the second motor controls the washing and disinfection compartment in translational motion to the rotating shaft to allow clean water to be sprayed evenly;
e) blowing air to dry the user's hands by controlling the third motor continues to spin the right circular disc to put the air pipe in place and blowing enough air to dry the user's hands; while the second motor controls the washing and disinfection compartment in translational motion on the rotating shaft to help dry the user's hands evenly;
f) drying the user's hands by controlling the third motor continues to rotate the right circular disc to put the wiper cluster in the sanitary position and the fourth motor spinning the wiper cluster to dry the user's hands; at the same time the second motor controls the washing and disinfection compartment in translational motion on the rotating shaft so that the wiper cluster dries the user's hands evenly;
g) spraying disinfectant by controlling the third motor continues to rotate the right circular disc to put the disinfectant solution pipe in place and spraying the disinfectant solution on the user's hands; while the second motor controls the washing and disinfection compartment in translational motion on the rotating shaft to allow the disinfectant to be spraying evenly;
h) considering whether the washing and disinfection compartment is performing hand massage; if YES, proceed to step i) below; if NO, terminate the cycle of hygiene and massage the user's hand;
i) massaging the user's hands by controlling the third motor continues to rotate the right circular disc to put the massage cluster in place and the sixth motor rotate the massage cluster for hand massage; while the second motor controls the washing and disinfection compartment moves forward on the rotating shaft so that the massage cluster can massage the user's entire hands.

\* \* \* \* \*